United States Patent [19]

Brown

[11] Patent Number: 5,532,154
[45] Date of Patent: Jul. 2, 1996

[54] MUTATED ALPHA VIRUS

[75] Inventor: Dennis T. Brown, Austin, Tex.

[73] Assignee: Research Development Foundation, Carson City, Nev.

[21] Appl. No.: 213,860

[22] Filed: Mar. 21, 1994

[51] Int. Cl.[6] .............................. C12N 7/04; C12N 7/00; C12N 15/40; A61K 39/12

[52] U.S. Cl. .................. 435/235.1; 435/236; 435/320.1; 435/240.2; 435/252.3; 435/254.2; 424/218.1; 935/65

[58] Field of Search .................................. 435/235.1, 236, 435/238, 320.1, 252.3, 240.2, 254.1; 424/204.1, 218.1, 221.1; 935/65

[56] References Cited

PUBLICATIONS

Murphy, B. R. et al. 1985. In *Virology*, ed. B. N. Fields et al, Raven Press, N.Y., pp. 349–370.
Rice, C. M. et al. 1987, *J. Virol.* vol. 61, pp. 3809–3819.
Ivanova, L. et al. 1993. *J. Virol.* vol. 67, pp. 2546–2551.
Anthony, R. P. et al. 1992. *Virology* vol. 190 pp. 330–336.
De, B. K. et al. 1988, *Vaccine* vol. 6, pp. 257–261.
Tidke, R. et al. 1987, *Vaccine* vol. 5 pp. 229–233.
Ryser, H. J. P. et al. 1994, *Proc. Natl. Acad. Sci. USA* vol. 91 pp. 4559–4563.
Omar, A. et al. 1989. *Virology* vol. 168 pp. 177–179.
Abell, B. A., et al. 1993, *J. Virol.* vol. 67 pp. 5496–5501.
Kajigaya, S. et al. 1989, *Proc. Natl. Acad. Sci.* USA vol. 86 pp. 7601–7605.

*Primary Examiner*—Mary E. Mosher
*Attorney, Agent, or Firm*—Benjamin Aaron Adler

[57] ABSTRACT

The present invention provides a composition of matter, comprising a non-infectious, mutated virus suitable for use in preparing a vaccine. A plasmid adapted for expression in a recombinant cell comprising DNA encoding non-infectious mutated virus protein and regulatory elements necessary for expression of said DNA in the cell. Also provided are methods of inhibiting the spread of infection of a virus comprising the step of contacting said virus with a compound that inhibits thiol-reductase/protein disulfide isomerase activity in said virus.

12 Claims, 6 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:1:

```
CGATGATGAT  TGGCGTAACT                    20
```

( 2 ) INFORMATION FOR SEQ ID NO:2:

( i ) SEQUENCE CHARACTERISTICS:
        ( A ) LENGTH: 24
        ( B ) TYPE: nucleic acid
        ( C ) STRANDEDNESS: double
        ( D ) TOPOLOGY: linear ( i i ) MOLECULE TYPE:
        ( A ) DESCRIPTION: other nucleic acid ( i i i ) HYPOTHETICAL: No ( i v ) ANTI-SENSE: No ( v i ) ORIGINAL SOURCE:
        ( B ) STRAIN:

```
        ( C ) INDIVIDUAL ISOLATE:
        ( D ) DEVELOPMENTAL STAGE:
        ( F ) TISSUE TYPE:
        ( G ) CELL TYPE:
        ( H ) CELL LINE:

( x i ) SEQUENCE DESCRIPTION: SEQ ID NO:2:

CGAAAAATCA   AATCCTGCGG   CTCC                24

( 2 ) INFORMATION FOR SEQ ID NO:3:

( i ) SEQUENCE CHARACTERISTICS:
            ( A ) LENGTH: 18
            ( B ) TYPE: nucleic acid
            ( C ) STRANDEDNESS: double
            ( D ) TOPOLOGY: linear ( i i ) MOLECULE TYPE:
            ( A ) DESCRIPTION: other nucleic acid ( i i i ) HYPOTHETICAL: No ( i v ) ANTI-SENSE: No ( v i ) ORIGINAL SOURCE:
            ( B ) STRAIN:
            ( C ) INDIVIDUAL ISOLATE:
            ( D ) DEVELOPMENTAL STAGE:
            ( F ) TISSUE TYPE:
            ( G ) CELL TYPE:
            ( H ) CELL LINE:

( i x ) FEATURE:

( x i ) SEQUENCE DESCRIPTION: SEQ ID NO:3:

CCAAAAATCA   AATCCTGC                         18
```

MUTATED ALPHA VIRUS

BACKGROUND OF THE INVENTION

1. Field of the Invention

The present invention relates generally to the fields of virology, immunology and protein chemistry. More specifically, the present invention relates to novel antiviral agents and novel methods of preparing vaccines.

2. Description of the Related Art

Viruses are complex three dimensional structures which serve as gene delivery systems. They are composed of an RNA or DNA genome packaged within a coat consisting of protein or a combination of proteins associated with a lipid containing membrane bilayer. In order to be sustained in nature, the virus genome is replicated by subverting the biochemical machinery of an appropriate host cell. This process of infection frequently results in the death of the host cell, a process which on a grand scale manifests itself as disease in the host plant or animal. The endproduct of the infection process is the release from the infected cell or tissue of hundreds to thousands of progeny virus particles which have the capability of infecting other cells, tissues or hosts. The virus genetic material is protected from destruction from environmental agents by the surrounding coat. While this coat must resist degradation by environmental factors, it must also disintegrate to release its genetic material as the virus infects a host cell.

The prior art is deficient in the lack of effective means of inhibiting the spread of certain viruses. The prior art is also deficient in the lack of effective means to ensure the non-infectivity of viruses used as vaccines. The present invention fulfills these longstanding needs and desires in the art.

SUMMARY OF THE INVENTION

In one embodiment of the present invention, there is provided a composition of matter comprising a non-infectious, mutated virus suitable for use in preparing a vaccine.

In another embodiment of the present invention, there is provided a recombinant plasmid adapted for expression in mammalian cells comprising DNA encoding a non-infectious mutated virus and regulatory elements necessary for expression of said DNA in the cell.

In yet another embodiment of the present invention, there is provided a virus associated thiol reductase/protein isomerase activity.

In still yet another embodiment of the present invention, there is provided a method of inhibiting the spread of infection of a virus comprising the step of contacting said virus with a compound that inhibits thiol-reductase/protein disulfide isomerase activity in said virus.

In another embodiment of the present invention, there is provided an anti-viral agent for inhibiting the spread of infection of a virus wherein said anti-viral agent inhibits thiol-reductase/protein disulfide isomerase activity in said virus.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 4A shows the glycoprotein in the mature virion has both functional and structural domains which are involved in membrane fusion and envelope integrity, respectively. FIG. 4B shows the conformational changes induced by the receptor-virus interaction or by exposure to low pH unmask critical disulfide bridges, favoring a subsequenct reshuffling of disulfide bridges. FIG. 4C shows that a reduction of critical disulfide bridges responsible for maintaining the protein-protein associations of the envelope disrupts the rigid protein icosahedral lattice, allowing subsequent fusion with a cellular membrane. The solid boxes indicate E1-E1 associations; the hatched boxes indicate the fusion peptide.

DETAILED DESCRIPTION OF THE INVENTION

Figure 1:
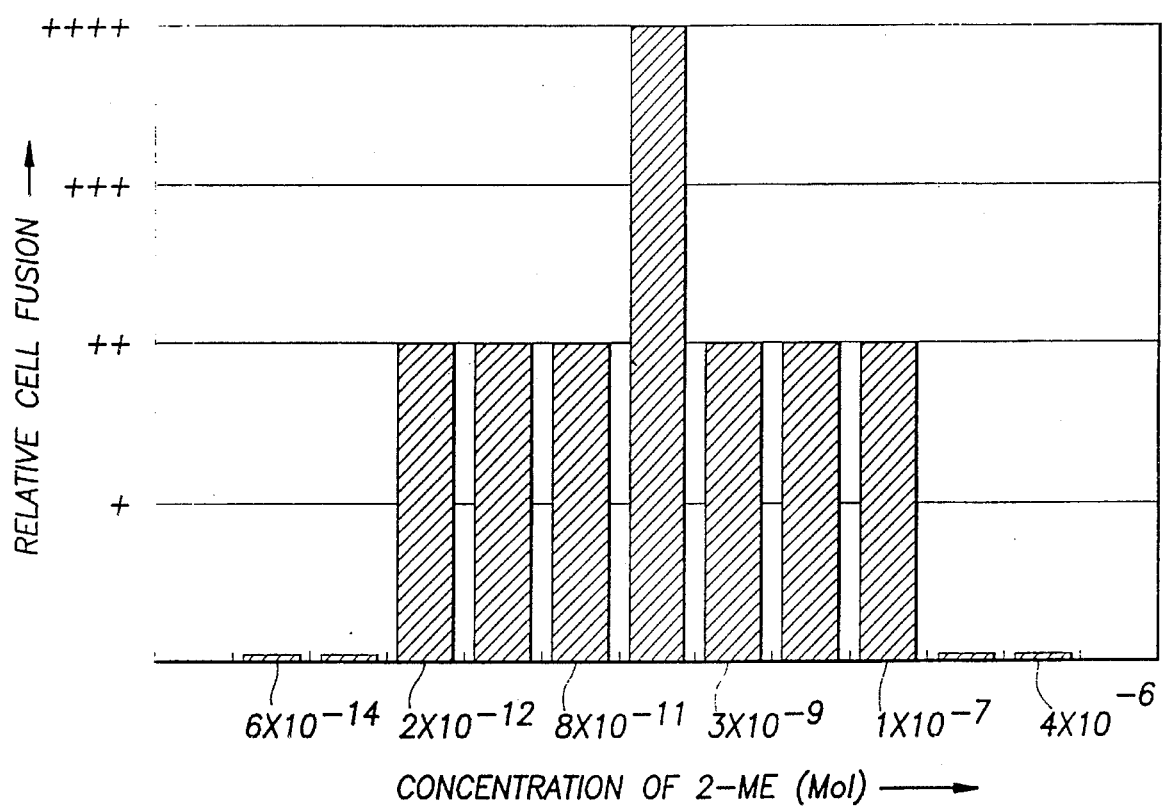
FIG. 1 shows the one step fusion from without (FFWO) in BHK cells at pH 5.3 in the presence of 2-mercaptoethanol (2-ME). Virus cell complexes were exposed to low pH fusion medium including various concentratons of the reducing agent 2-ME as described below. Fusion was scored as described below.

In the present invention, using the membrane-containing virus Sindbis, (the prototype of the Alpha viruses), it is shown that this virus has, as a component of one of its two membrane-coat associated glycoproteins, a protein domain which, in its structure and function, is a homolog of proteins having known thiol-reductase/protein disulfide isomerase activity. The present invention also shows that a model Corona virus (Mouse Hepatitis Virus) has the mechanism of infection similar to that described for Sindbis virus and that thus, this mechanism is employed by other viruses to infect host cells.

The surface proteins of many animal viruses contain complex disulfide bridges which may stabilize the particles and which have to be broken in order for the process of infection and release of the viral genome to take place. The present invention has identified a mechanism which explains a critical process that takes place as these viruses infect hosts. This unique and previously undescribed activity illustrates a new strategy for controlling virus infection and for the production of vaccines.

The present invention shows that a virus itself possesses the ability to reduce its disulfide bridges after attaching to an appropriate host cell receptor. The interaction of the virus structural protein with the host receptor initiates conformational changes in the virus allowing the reductive event to take place.

The present invention illustrates that a thiol-disulfide exchange is critical to the infection of cells by Alpha and Corona viruses. In the case of Alpha viruses, this reductive event is carried out by a thiol-reductase/disulfide isomerase activity located in the virus itself. Many viruses (including HIV) contain disulfide bridges which have been shown to be essential for the structure and assembly of the virus. The structural integrity of the virus is dependent upon these disulfide bridges which must be broken in order for the process of host infection to proceed. The mutant of the present invention represents a new way to produce a non-infectious virus to use as vaccines. The mutant viruses of the present invention are superior to other vaccines in that they do not require inactivation by chemical or physical treatments. They therefore present the immune system with antigens more closely identical to those existing in the infectious virion. The present invention also describes ways to identify chemical agents which can interfere with the endogenous thiol-reductase activity thus serving as drugs preventing the spread of virus infection. The virus associated thiol-reductase is homologous to those of known enzymes. Thus, agents capable of blocking one of these activities in one virus would block the activity in other viruses.

The present invention is directed to a composition of matter comprising a non-infectious, mutated virus suitable for use in preparing a vaccine. Generally, the virus is mutated by substituting an amino acid for a conserved cysteine amino acid. A person having ordinary skill in this art would readily recognize that there are a small number of amino acids which could be substituted for cysteine in the methods and compositions of the present invention. For example, the methods and compositions of the present invention replace the specific amino acid cysteine with serine. Preferably, the amino acid replaced to create the mutated viruses of the present invention are those conserved cysteines that are in a domain of the virus protein responsible for thiol-reductase/protein disulfide isomerase activity.

It is intended that the methods of the present invention and the compositions provided by the present invention may involve any known virus. Preferably, the mutated virus is a mutant of a virus selected from the group consisting Alphaviruses and Corona viruses. A representative example of an Alphavirus is the Sindbis virus. A representative example of a Corona virus is the Mouse Hepatitis virus. A representative example of a mutated Sindbis virus is the mutant E1-SER$^{62}$.

The present invention provides for novel plasmids adapted for expression in cells comprising recombinant DNA encoding non-infectious mutated virus and regulatory elements necessary for expression of said DNA in the cell. The plasmids of the present invention may be adapted for expression in bacterial, yeast, insect or mammalian cells. Representative examples of yeast are Saccaromyces, Pichia and Kluyveromyces. Representative examples of bacterial cells are E. coli, Bacillus subtilis, Salmonella typhimurium, Pseudomonas, Streptomyces and Staphylococcus. Representative examples of mammalian cells are BHK-21, Vero, HeLa and Chinese Hamster Ovary (CHO) cells.

The plasmid of the present invention contains a mutated virus of the present invention. Preferably, the virus is an Alphavirus and a Corona virus. A representative example of a mutated Alphavirus is a mutated Sindbis virus. A representative example of the mutated Sindbis virus is the mutant E1-SER$^{62}$.

The present invention also provides for novel transfected cells. Representative examples of transfected cells include a transfected cell comprising the plasmid of claim 7 and a transfected cell comprising the plasmid of claim 14. In addition, the present invention also discloses non-infectious, mutated viruses produced by the transfected cells of the present invention.

The present invention also includes a method of inhibiting the spread of infection of a virus comprising the step of contacting said virus with a compound that inhibits thiol-reductase/protein disulfide isomerase activity in said virus. Also provided is an anti-viral agent for inhibiting the spread of infection of a virus wherein said anti-viral agent inhibits thiol-reductase/protein disulfide isomerase activity in said virus. Following the teachings of the present invention, a person having ordinary skill in this art would readily be able to devise additional compounds which inhibit thiol-reductase/protein disulfide isomerase activity in an virus of interest.

The following examples are given for the purpose of illustrating various embodiments of the invention and are not meant to limit the present invention in any fashion.

EXAMPLE 1

Cells, Virus and Media

BHK-21 cells were cultured at 37° C. in Eagle's minimal essential medium (MEM) supplemented with 10% fetal calf serum (GIBCO), 5% tryptose phosphate broth and 2 mM L-glutamine. Heat resistant Sindbis virus (SVHR), originally provided by E. Pfefferkorn (Darmouth Medical College) was passaged at low multiplicity and titrated on BHK-21 cells as described by Renz and Brown, *J. Virol.* 19:775–781 (1976).

EXAMPLE 2

Sindbis virus mediated FFWO

Variations of Sindbis virus mediated FFWO were 1,000 PFU of SVHR per cell to BHK monolayers at 4° C. for 60 minutes. The viral inoculum was then replaced with 37° C. fusion medium, consisting of Eagle's MEM without bicarbonate, 10 mM MES [2(N-morpholino)ethanesulfonic acid] and 10 mM HEPES (N-2-hydroxyethylpiperazine-N'-2-ethanesulfonic acid) adjusted to pH 5.3 with and without various concentrations of 2-mercaptoethanol (2-ME). Fusion was assayed with a phase-contrast microscope after 5 hours of incubation at 37° C. and scored as follows: −, no fusion; +, less than 25% of cells fused; ++25 performed. Briefly, FFWO at low pH was induced by adsorbing to 50% of cells fused; +++50–95% of cells fused; ++++, more than 95% of cells fused. The degree of fusion was calculated as 1-(number of cells/number of nuclei). Two pH step FFWO was induced as described above except that various multiplicities of SVHR were used, the fusion medium contained 0.05 nM 2-ME and the virus-cell complexes were returned to growth medium after 5 minutes of incubation in low pH fusion medium. The monolayers were photographed under phase contrast illumination after one hour of incubation at 37° C. and scored as described above.

EXAMPLE 3

Drugs

DTNB was solubilized in serum-free MEM. DTNB concentrations as high as 5 mM did not affect cell viability, as assayed by incorporation of [$^3$H]uridine into trichloroacetic acid (TCA)-precipitable cellular RNA, trypan blue exclusion, or neutral red uptake. Direct effects of DTNB on Sindbis virus infectivity were determined by incubating the reagent with the virus for various periods of time, quenching the incubation by serial dilution into phosphate-buffered saline containing 3% fetal calf serum and titrating on BHK cells in a standard plaque assay as described by Renz and Brown, *J. Virol.* 19:775–781 (1976).

EXAMPLE 4

Penetration assays

Viral RNA synthesis was assayed by determining incorporation of [3H]uridine into TCA-precipitable material in BHK cells treated with 4 μg of dactinomycin per ml for 90 minutes prior to infection and maintained in dactinomycin throughout. Monolayers of equal numbers of BHK cells were treated with 1 mM DTNB for 30 minutes at 37° C. at three different times with respect to a one hour adsorption of 5 PFU of SVHR per cell at 4° C. After adsorption, all of the monolayers were washed with serum-free MEM and incubated at 37° C. to allow penetration of the adsorbed virus. The 30 minute DTNB treatments were done either immediately prior to adsorption, during the period of penetration at 37° C., or immediately after this penetration period. After the DTNB treatments, the monolayers were washed. [3H] uridine (10 μCi/ml) was added 90 minutes after the period of penetration, and at 5 hours, the monolayers were lysed with sodium dodecyl sulfate and precipitated with 10% ice-cold TCA and radioactivity was counted. Penetration was also assayed by plaque formation on BHK monolayeers that had been exposed to 1 mM DTNB for 60 minutes under the treatment conditions described above. Plaque formation was determined as described by Renz and Brown, *J. Virol.* 19:775–781 (1976).

EXAMPLE 5

FFWO at low pH

The rate of Sindbis virus-mediated FFWO is dependent upon the pH to which the cells are returned after exposure to low pH Edwards and Brown, *J. Gen Virol.*, 67:377–380 (1986). Fusion proceeds faster at higher pHs and does not occur at the low pH threshold of 5.3 required to establish conditions for fusion upon a return to neutrality. Thiol-disulfide exchange reactions are similarly pH dependent in that the reaction rates are directly affected by pH, occurring efficiently only in neutral to alkaline environments as shown by Feener et al., *J. Biol. Chem.* 265:18780–18785 (1990). If reduction of critical viral disulfide bridges is necessary to disrupt the rigid envelope protein lattice prior to membrane fusion, it would be blocked at low pH.

To illustrate the role of such a reductive event in Sindbis virus-mediated FFWO of BHK cells, fusion was attempted at low pH in the presence of the reducing agent 2-ME. Unlike DTT and cysteine, 2-ME is an effective reducing agent at pH 5.0 and above (Torchinskii, Sulfhydryl and Disulfide Groups of Proteins, Plenum Publishing, N.Y. 1974). Treatment with a wide range of 2-ME concentrations was found to induce FFWO at pH 5.3, although this range of concentrations varied. 2-ME induced fusion at low pH is highly sensitive to a number of factors, including the passage number of the cells and the degree of confluency of the monolayers, which are not as critical to the process of fusion after a return to neutral pH. Treatment of monolayers with 2-ME in the absence of virus and incubation of virus cell complexes at pH 5.3 in the absence of 2-ME do not induce fusion. The extremely low concentrations of reducing agent necessary to induce FFWO suggest that the critical disulfide bridges being reduced are highly strained. High concentrations of 2-ME do not promote fusion, possibly because the viral envelope is destroyed before the fusion event can occur. That Sindbis virus-mediated FFWO occurs at low pH in the presence of low concentrations of 2-ME is consistent with the reduction of critical vital disulfide bridges being important for virus-cell fusion. In addition, it may explain the FFWO requirement for a return to a neutral pH environment.

EXAMPLE 6

Effect of 2-ME on the multiplicity requirement for FFWO

Figure 2:
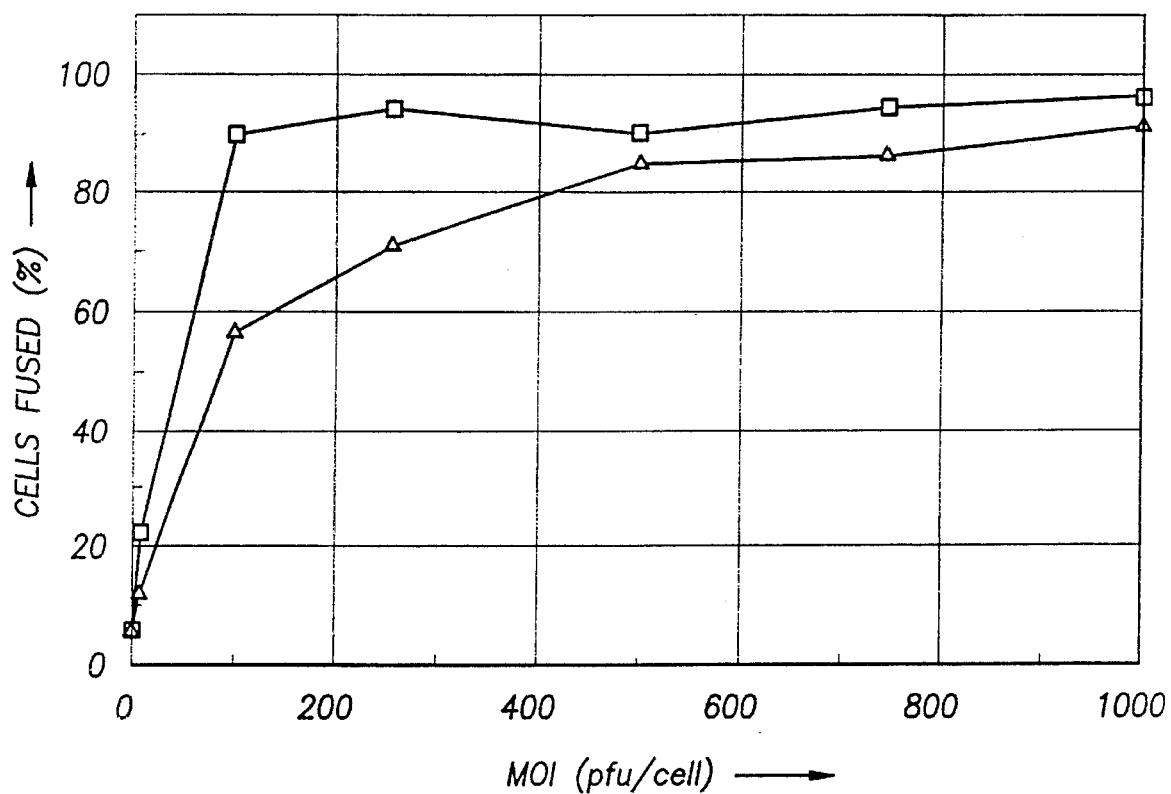
FIG. 2 shows the multiplicity (MOI) dependence of two-step FFWO in BHK cells exposed to 2-ME. Virus-cell complexes were exposed to low pH fusion medium with 0.05 nM 2-ME (squares) or without 2-ME (triangles) for five minutes, returned to neutral pH and scored for fusion as described below.

2-ME induction of fusion at low pH implies that the efficiency of Sindbis virus induced FFWO depends upon a reductive event. FIG. 2 shows the effect of 2-ME on the multiplicity requirement for typical Sindbis virus-mediated FFWO. This reducing agent, when present during the brief exposure of the virus-cell complexes to low pH during FFWO, increased the efficiency of fusion after a return to neutrality. Optimal fusion in the 2-ME-treated monolayers was obtained at multiplicities as low as 100 PFU/cell, whereas multiplicities of 500 to 1,000 PFU/cell were typically required in the absence of 2-ME treatment. The high-multiplicity requirement for FFWO must in part reflect the frequency with which attaching virions form multiple cell contacts, a steric requirment for the cell-virus-cell fusion event. If this fusion phenomenon is dependent upon a thiol-disulfide exchange reaction, the high multiplicity requirement may also reflect the frequency with which the critical viral disulfide bridges associate with appropriate thiol donors. An increase in the availability of thiols due to the exogenous reducing agent 2-ME would reduce the number of virions required to produce maximal cell-cell fusion. This is supported by the decrease in multiplicity required for maximal fusion after brief exposure to 2-ME.

EXAMPLE 7

Figure 3:
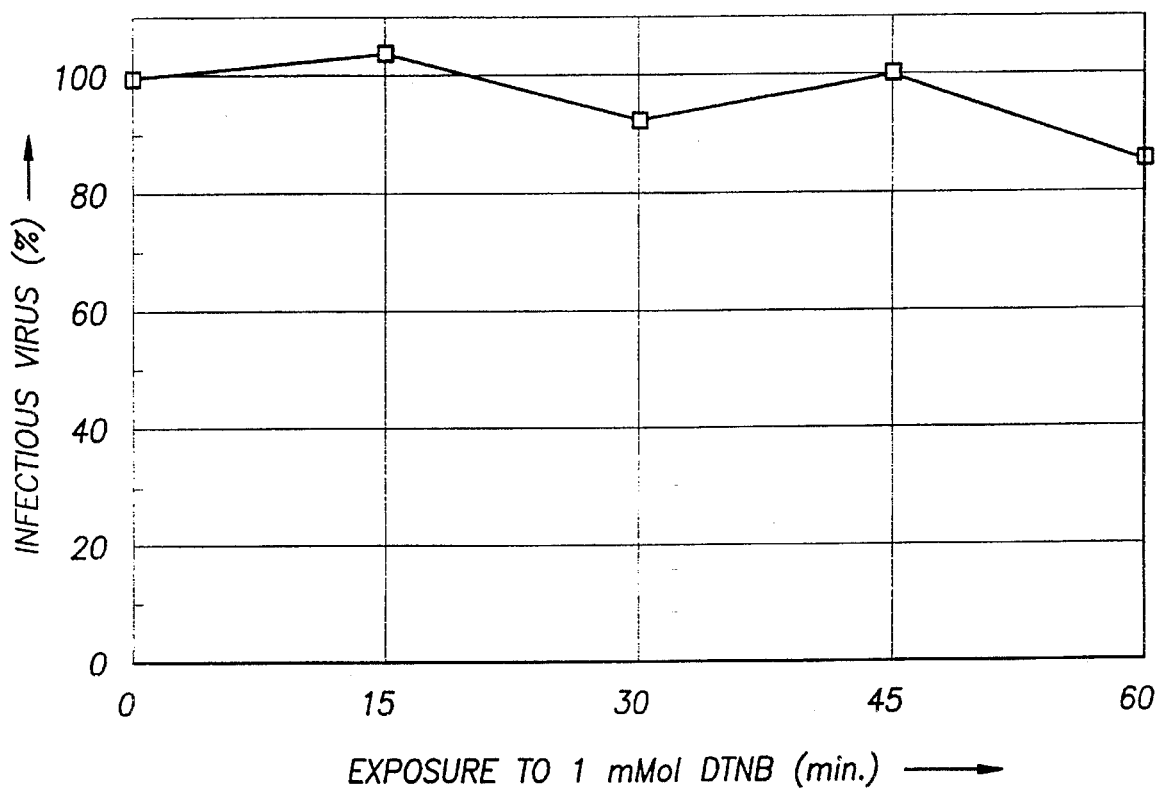
FIG. 3 shows the direct effect of DTNB on Sindbis virus infectivity. Virus was exposed to 1 mM DTNB for various periods of time and remaining infectious virus was titrate on BHK monolayers. Infectious virus is expressed as a percentage of that in the untreated control.

Thiol-disulfide exchange reactions in Sindbis virus penetration of BHK cells The present invention shows that the reduction of disulfide bridges in the rigid envelope protein lattice of Sindbis virus is requred for membrane fusion during entry. DTNB is a membrane-impermeable sulfhydryl-blocking reagent that covalently modifies sulhydryls via a thiol-disulfide exchange reaction. As it does not directly affect Sindbis virus infectivity (FIG. 3) or BHK cell viability, DTNB is an excellent reagent to illustrate thiol-disulfide exchange reactions occurring at the plasma membrane during Sindbis virus penetration.

EXAMPLE 8

Effect of DTNB on viral penetration

The effect of DTNB on viral penetration at low multiplicities of infection was assayed by [$^3$H]uridine incorporation into vital RNA under three treatment conditions as described in Example 4 and Table I. In the presence of dactinomycin, BHK cells were treated for 30 minutes with 1 mM DTNB either prior to adsorption of the virus at 4° C., during penetration of the virus at 37° C., or immediately after the penetration period. In each case, viral RNA was assayed at 5 hours after the penetration period by measuring the incorporation of [3H]uridine into TCA precipitable material. DTNB treatment of cells prior to infection had a slight inhibitory effect on viral RNA synthesis, while treatment during virus penetration inhibits RNA production to approximately 40% of control levels. The decrease in RNA synthesis seen with treatment of the cells prior to infection likely results from a failure to remove all of the drug prior to infection. Treatment with DTNB after an initial period of penetration has a limited inhibitory effect. However, the depression of RNA synthesis after this treatment may be due to the fact that Sindbis virus infection increases the permeability of cells, allowing some membrane impermeable reagents direct access to the cytoplasm, where they can have secondary effects.

The effect of DTNB on Sindbis virus penetration was also determined by assaying plaque formation as shown in TABLE I. In the studies shown in TABLE I, virus was adsorbed to equal numbers of BHK cells for one hour at 4° C., replaced in warm MEM and incubated at 37° C. to allow penetration. Cells were treated for 30 minutes (A) or 60 minutes (B) with 1 mM DTNB at the indicated times. The monolayers were then washed to remove the drug prior to further incubation at 37° C. in DTNB free medium. Results are the averages of five independent experiments plus or minus standard deviation. Total viral RNA was determined five hours after the cells were warmed to 37° C. to initiate penetration. Monolayers were overlaid with agarose and stained with neutral red 48 hours after infection.

Pretreatment of the cells with DTNB results in a slight inhibition of plaque formation, while treatment during the period of infection inhibits plaque formation to approximately 46% of untreated control levels. Again, the decrease in plaque formation seen when monolayers were treated with DTNB prior to infection probably results from an inability to remove all of the reagent prior to infection. Treatment with DTNB postinfection has no inhibitory effect on plaque formation, which is consistent with the depression in RNA levels with DTNB treatment after infection was not due to a direct effect on penetration of the virus. Although paradoxical, the slightly higher number of plaques found in cell cultures treated after infection was highly reproducible.

TABLE I

| Effect of DTNB on penetration of cells be Sindbis virus | | |
|---|---|---|
| Determination | Treatment time | % of control |
| Viral RNA synthesis | Before penetration | 82 ± 11 |
| | During penetration | 40 ± 10 |
| | After penetration | 81 ± 13 |
| Plaque formation | Before penetration | 80 ± 11 |
| | During penetration | 46 ± 10 |
| | After penetration | 110 ± 13 |

The interesting observation that Sindbis virus penetration is most effectively inhibited by DTNB when the reagent is present during the period of infection suggests that targeted thiol groups are unmasked during entry though a cooperative interaction between the virus and its receptor. The cooperative and rapid nature of this interaction may create circumstances in which DTNB cannot efficiently compete with a viral disulfide bridge undergoing a thiol-disulfide exchange reaction. Such reactions have rapid reaction rates, about $10^{-6}$ second at pH 8.0 and an inefficiency in alkylating the critical thiols would result in an inability to completely block Sindbis virus penetration.

Figure 4:
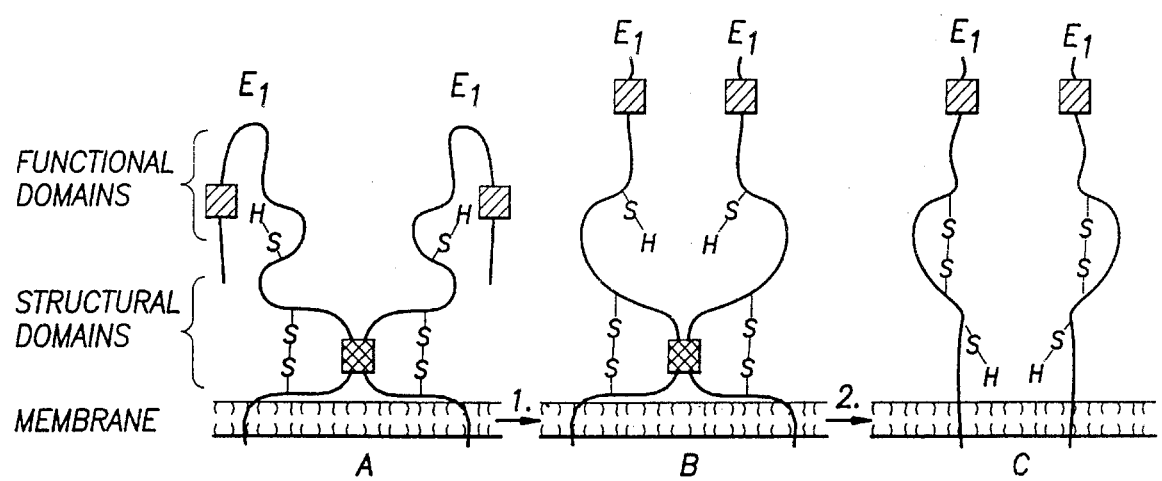
FIG. 4 depicts conformational changes in E1 during Sindbis virus membrane penetration and low pH induced membrane fusion.

FIG. 4 depicts conformational changes in E1 during Sindbis virus membrane penetration and low pH induced membrane fusion. FIG. 4A shows the glycoprotein in the mature virion has both functional and structural domains which are involved in membrane fusion and envelope integrity, respectively. FIG. 4B shows the conformational changes induced by the receptor-virus interaction or by exposure to low pH unmask critical disulfide bridges, favoring a subsequenct reshuffling of disulfide bridges. FIG. 4C shows that a reduction of critical disulfide bridges responsible for maintaining the protein-protein associations of the envelope disrupts the rigid protein icosahedral lattice, allowing subsequent fusion with a cellular membrane. The solid boxes indicate E1-E1 associations; the hatched boxes indicated fusion peptide.

Fusion of enveloped viruses with cellular membranes during penetration is protein mediated as are intracellular and intercellular fusion events. The exposure of a fusion domain in the envelope protein E1 is involved in the fusion of Alphaviruses with cellular membranes. In addition, the present invention shows that the disulfide bridge stabilized E1-E1 associations of the envelope must be disrupted for membrane fusion to occur. The most likely mechanism for disassembly of the Sindbis virus envelope protein-protein interactions during penetration is the reduction of these stabilizing disulfide bridges via thiol-disulfide exchange reactions.

A thiol disulfide exchange reaction occurs by the nucleophilic attack of an ionized thiol on a disulfide bridge and is highly dependent on environmental pH, the pKa of the thiol, and steric hindrince. Cysteine-mediated thiol-disulfide exchange reactions thus require neutral to alkaline pHs. FFWO mediated by the HR strain of Sindbis virus requires exposure to pH 5.3 with a subsequent return to pHs greater than 6 to induce fusion. The rate of fusion increases as the pH to which the virus-cell complexes are returned increases and fusion does not occur at the low pH threshold required for fusion. Likewise, rapid disassembly of the viral envelope by DTT also requires brief exposure to pH 5.3 followed by a return to neutral pH. These observations implicate a definite role for a neutral pH environment in the thiol-disulfide exchange reaction. The teachings of the present invention illustrate that for virus-cell fusion, thiol disulfide exchange reactions are critical to the fusion process.

The process of low pH mediated FFWO differs from the process of infection in that it requires high multiplicities of virus and is protein receptor independent. However, both processes must supply a mechanism for the disruption of the envelope protein lattice prior to fusion. The present invention shows that both events are similarly dependent upon a thiol-disulfide exchange reacton. Addition of very low concentrations of the reducing agent 2-ME (which, unlike DTT and biological thiols, reduces efficiently at pH 5.3) promotes cell fusion in an acidic environment, suggesting that the chemical reduction of critical disulfide bridges can induce fusion in an otherwise unfavorable reductive environment. The extremely low concentration of 2-ME needed to promote this fusion imply that the critical disulfide bridges being reduced are in very strained conformations. Low pH induced conformational changes in the envelope proteins could be responsible for exposing these strained critical disulfide bridges and may explain the very rapid nature of in vitro DTT-mediated virus disassembly following low pH exposure.

The process of Sindbis virus penetration of host cell is receptor dependent and several possible receptors have been identified. The interaction of the virus with a cell surface receptor at neutral pH induces conformational changes in the viral glycoprotein which precede penetration. The present invention shows that a cooperative interaction between the receptor and the virus induces conformational changes which allow the reduction of critical disulfide bridges within the envelope proteins by thiol-disulfide exchange reactions. The progression from the receptor induced conformational changes to the disruption of the envelope protein lattice and fusion likely proceeds very rapidly. The fact that the stabilizing disulfide bridges and critical thiols are inaccessible to molecules such as DTT and DTNB while in the native state, combined with the extremely rapid rate at which the reductive event occurs after the receptor induced conformational changes may explain the inefficiency of DTNB in blocking this process. Thiols mediating the reductive events may reside either in the receptor protein or within the virus itself. In the latter case, a reshuffling of disulfide bridges following attachment would result in the required disruption of the envelope protein lattice. In such a model, the interaction of the virus with an appropriate receptor alters the conformation of E1, favoring a reshuffling of disulfide bridges via thiol-disulfide exchange reactions. This reshuffling of disulfide bridges leads to disruption of the rigid protein-protein associations in the envelope allowing subsequent fusion of the viral envelope with the plasma membrane.

EXAMPLE 9

Production of the mutant E1-SER$^{62}$

The structure of proteins which have known thiol-reductase/protein disulfide isomerase activity were gathered from the Gene bank. Although there was no absolutely conserved amino acid sequence in the functional domains of these proteins, the "donor" cysteine was invariably located in a protein domain containing positively charged-basic amino acids. Indeed, the thiol-reductase activity in these proteins can be increased by increasing the net positive charge of this domain. The amino acid sequences of the E1 glycoproteins of all the known Alphaviruses were examined. This inspection revealed two cysteines (62&79) which were conserved and were located in domains typical of the positive charged domains of known thiol-reductase activities. Thus, a mutation eliminating one of these cysteines renders the virus non-infectious by eliminating a thiol-reductase activity associated with this domain.

The mutation of cysteine to serine at position 62 in the sequence of the E1 glycoprotein of Sindbis virus was produced by megaprimer PCR mutagenesis as described by Liu and Brown, J. Cell. Biol., 120:877–883 (1993). Two primers, representing sequences 9760–9779 (primer A) and nucleotides 10445 through 10436 (primer B) in the nucleotide sequence of Sindbis Toto 1101 were constructed as "end primers".

primer A=5'-CGATGATGATTGGCGTAACT-3' primer B=5'-CGAAAAATCAAATCCTGCGGCTCC-3'

The "mutant primer" with a G to C base change consisted of nucleotide 10236 through 10259

5'- CCAAAAATCAAATCCTGC-3'

G (wild type)

The megaprimer was generated by adding mutant primer and primer B to the template Toto producing a first product: nucleotide 10236 through 10445 with a mutation and an SPL I cleavage site at 10381.

The mutant megaprimer was elongated to incorporate a second restriction enzyme site by combining primer A with the product of the first PCR reaction. The template was a purified fragment of Toto 1101 consisting of nucleotide 8571–10381 produced by digestion with restriction enzymes STU I and SPL I. The second product was nucleotide 9760 through 10445 with the required mutation and BSIW (NT 9804) and SPL I (NT 10381) cleavage sites.

Figure 5:
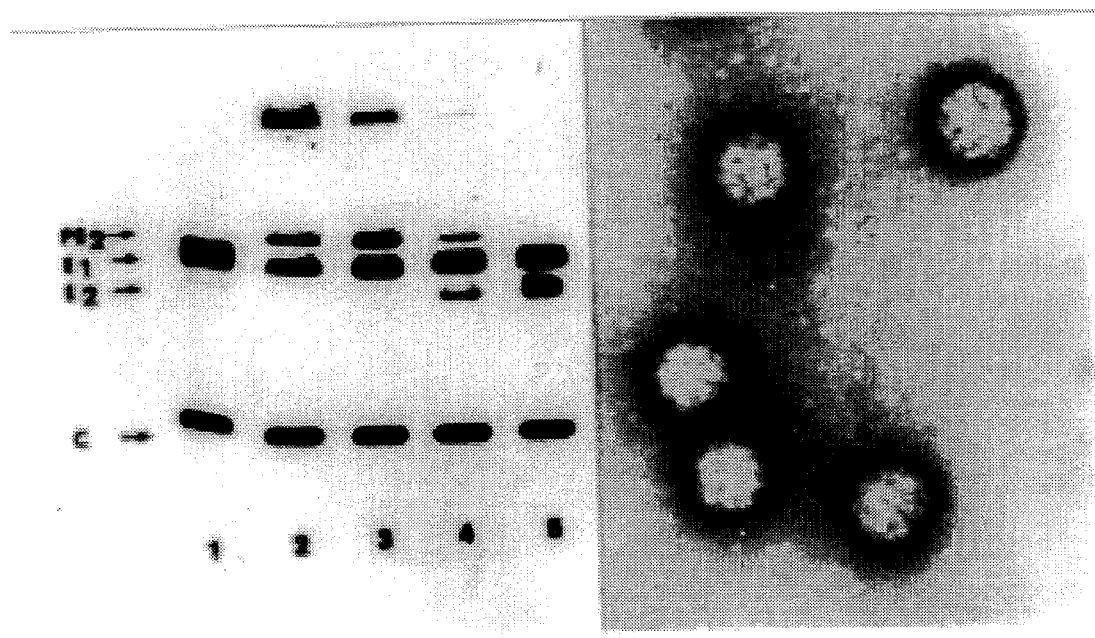
FIG. 5 shows the Sindbis mutant E 1-ser$^{62}$. Cells were labeled at 5 hours post-infection with $^{35}$S-methionine/cysteine and chased for 0 (lane 1), 5 (lane 2), 10 (lane 3), 20 (lane 4) minutes in the presence of cycloheximide. Lysate of cells were imuno-precipitated with anti-serum produced against purified virus. Ser$^{62}$ produces virus proteins PE2, E1, E2 and C and that PE2 is chased into E2. The electron micrograph shows virions concentrated from the media of transfected cells and purified by density gradient centrifugation. The protein content of radioactive mutant virus is shown in lane 5.

The enzymes BSIW and SPL I were used to cut NT's 9804 through 10381 form Toto 1101 and second PCR product. The mutant product described above was ligated into Toto 1101 in place of the wild type sequence resulting in a plasmid containing Sindbis virus sequence with a base substitution of serine for cysteine at position 62. This plasmid was amplified in E. coli and RNA produced from the plasmid by in vitro transcription was used to transfect BHK-21 (mammalian) cells to produce the virus shown in FIG. 5.

This clone of the present invention uses an SP6 promoter to produce messenger RNA from the clone which is identical to the RNA of the intact virus when the clone is used to program an in vitro transcription reaction. When the RNA product of this reaction was transfected into cultured mammalian cells, it resulted in an infection which proceeded in a fashion identical to that established by intact virus (see FIG. 5). Mature viruses which are structurally and biochemically indistinguishable (with the exception of the serine substitution) from normal virus were produced. These virus particles were however found to be completely non-infectious by standard assay procedures. The present invention demonstrates that a conformational change in the structure of the virus membrane glycoproteins takes place when the virus interacts with a cell surface receptor. This conformational change is a prerequisite for the process of membrane penetration. The conformational change exposes a thiol group which can be chemically reacted with the thiol blocking agent dithionitrobenzene. The reaction of this agent with this thiol blocks the process of virus penetration. The target critical thiol is either in the cell surface receptor protein or in the virus membrane glycoprotein.

The present invention provides direct genetic evidence that the thiol donor and disulfide target both reside in the virus glycoprotein E1 and that the protein domain surrounding and including cysteine 62 in the E1 sequence has an activity similar to that of known thiol-reductase/protein isomerase.

EXAMPLE 10

Corona Virus

Figure 6:
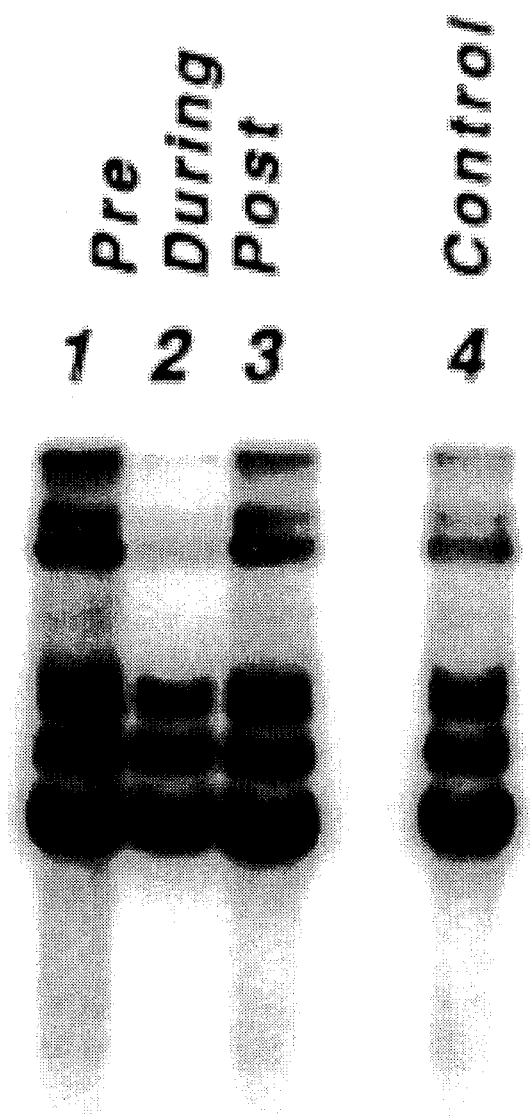
FIG. 6 shows the effect of the thiol blocking agent DTNB on the infection of cells by the model Corona virus, mouse hepatitis virus (MHV).

The effect of the thiol blocking agent DTNB on the infection of cells by the model Corona virus, Mouse Hepatitis Virus is shown in FIG. 6. Tissue cultured cells were treated with DTNB prior to, during or after virus infection as indicated. The virus RNA was extracted and the virus RNA from an equal number of cells was separated by gel electrophoresis. Densitometer tracings reveal that the amount of the 6 species of virus RNA was reduced by 50% when DTNB was present while infection was occurring. DTNB did not significantly alter the amount of RNA produced in the pre- and post-treatment experiments compared to the control in which no DTNB was added (extreme right lane). Thus, the Mouse Hepatitis virus parallels that found with the Sindbis virus and shows that a thiol-disulfide exchange reaction is critical for infection of cells by the membrane containing Corona viruses.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

---

What is claimed is:

1. A non-infectious, mutated alphavirus suitable for use in preparing a vaccine, wherein said virus is mutated by replacing a conserved cysteine amino acid with a different amino acid in the E1 protein and wherein said conserved cysteine is in a domain of the virus protein responsible for thiol-reductase/protein disulfide isomerase activity.

2. The mutated alphavirus off claim 1, wherein said mutated alphavirus is a mutated Sindbis virus.

3. The mutated virus of claim 2, wherein said mutated Sindbis virus is the mutant E1-SER$^{62}$.

4. A recombinant DNA plasmid encoding non-infectious mutated alphavirus, wherein said virus is mutated by replacing a conserved cysteine amino acid in the E1 protein with a different amino acid, and wherein said conserved cysteine is in a domain of the virus protein responsible for thiol-reductase/protein disulfide isomerase activity.

5. The plasmid of claim 4, wherein said mutated alphavirus is a mutated Sindbis virus.

6. The plasmid of claim 5, wherein said mutated Sindbis virus is the mutant E1-SER$^{62}$.

7. A transfected cell comprising the plasmid of claim 4.

8. The transfected cell of claim 7, wherein said cell is selected from the group consisting of bacterial, yeast, insect, and mammalian cells.

9. The transfected cell of claim 8, wherein said cell a mammalian cell selected from the group consisting of BHK-21, HELA, CHO, and Vero.

10. A transfected cell comprising the plasmid of claim 6.

11. The transfected cell of claim 10, wherein said cell is selected from the group consisting of bacterial, yeast, insect, and mammalian cells.

12. The transfected cell of claim 11, wherein said cell a mammalian cell selected from the group consisting of BHK-21, HELA, CHO, and Vero.

* * * * *

UNITED STATES PATENT AND TRADEMARK OFFICE
CERTIFICATE OF CORRECTION

PATENT NO. : 5,532,154
DATED : July 2, 1996
INVENTOR(S) : Dennis T. Brown

It is certified that error appears in the above-identified patent and that said Letters Patent is hereby corrected as shown below:

In Column 2, line 23, "titrate" should read --titrated--.

In Column 2, line 31, please insert the word --that-- between the words "shows" and "the".

In Column 2, line 67, please delete the word "that" at the end of the line after the word "and".

In Column 3, line 24, "HIV)contain" should read --HIV) contain--.

In Column 3, line 59, please insert the word --of-- between the words "consisting" and "Alphavirus".

In Column 4, line 7, please italicize the words "Pseudomas, Streptomyces and Staphylococcus".

In Column 5 line 61, please insert a comma between the words "pH" and "Edwards".

UNITED STATES PATENT AND TRADEMARK OFFICE
CERTIFICATE OF CORRECTION

PATENT NO. : 5,532,154
DATED : July 2, 1996
INVENTOR(S) : Dennis T. Brown

It is certified that error appears in the above-identified patent and that said Letters Patent is hereby corrected as shown below:

In Column 13, line 43, "off" should read --of--.

In Column 14, line 43, please insert the word --is-- between the words "cell" and "a".

Signed and Sealed this

Twenty-seventh Day of February, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO.   : 5,532,154
DATED        : July 2, 1996
INVENTOR(S)  : Brown

It is certified that error appears in the above-identified patent and that said Letters Patent is hereby corrected as shown below:

Column 1,
Line 1, please insert -- The United States government may own certain rights to this invention pursuant to grant number AI 14710 from the National Institutes of Health. --.

Column 2,
Line 23, "titrate" should read -- titrated --.
Line 31, please insert the word -- that -- between the words "shows" and "the".
Line 67, please delete the word "that" at the end of the line after the word "and".

Column 3,
Line 24, "HIV)contain" should read -- HIV) contain --.
Line 59, please insert the word -- of -- between the words "consisting" and "Alphavirus".

Column 4,
Line 7, please italicize the words "Pseudomas, Streptomyces and Staphylococcus".

Column 5,
Line 61, please insert a comma between the words "pH" and "Edwards".

Column 13,
Line 43, "off" should read -- of --.

Column 14,
Line 43, please insert the word -- is -- between the words "cell" and "a".

Signed and Sealed this

Twenty-fifth Day of October, 2005

JON W. DUDAS
*Director of the United States Patent and Trademark Office*